US011998245B2

(12) United States Patent
Oglaza et al.

(10) Patent No.: US 11,998,245 B2
(45) Date of Patent: *Jun. 4, 2024

(54) SYSTEM INCLUDING AN INTRAVERTEBRAL IMPLANT AND A PEDICLE FIXATION FOR TREATING A VERTEBRAL BODY

(71) Applicant: Stryker European Operations Limited, Carrigtwohill (IE)

(72) Inventors: Jean-François Oglaza, Portage, MI (US); Yves-Alain Ratron, Grenoble (FR); Gianluca Maestretti, Wallenreid (CH)

(73) Assignee: Stryker European Operations Limited, Carrigtwohill (IE)

( * ) Notice: Subject to any disclaimer, the term of this patent is extended or adjusted under 35 U.S.C. 154(b) by 64 days.

This patent is subject to a terminal disclaimer.

(21) Appl. No.: 17/723,974

(22) Filed: Apr. 19, 2022

(65) Prior Publication Data

US 2022/0240987 A1 Aug. 4, 2022

Related U.S. Application Data

(63) Continuation of application No. 16/801,842, filed on Feb. 26, 2020, now Pat. No. 11,344,335, which is a
(Continued)

(30) Foreign Application Priority Data

Dec. 23, 2013 (FR) ...................................... 1363467

(51) Int. Cl.
*A61B 17/70* (2006.01)
*A61B 17/84* (2006.01)
(Continued)

(52) U.S. Cl.
CPC .......... *A61B 17/7032* (2013.01); *A61B 17/70* (2013.01); *A61B 17/844* (2013.01);
(Continued)

(58) Field of Classification Search
CPC ............ A61B 17/7032; A61B 17/7034; A61B 17/7035; A61B 17/7038
See application file for complete search history.

(56) References Cited

U.S. PATENT DOCUMENTS

| 4,796,612 A | 1/1989 | Reese |
| 4,932,975 A | 6/1990 | Main et al. |

(Continued)

FOREIGN PATENT DOCUMENTS

| AU | 705930 B2 | 6/1999 |
| CN | 1162349 A | 10/1997 |

(Continued)

OTHER PUBLICATIONS

Youtube, "VCFix Spinal System Video", https://www.youtube.com/watch?v=_JtphuwHkBs, Sep. 30, 2021, 3 pages.
(Continued)

*Primary Examiner* — Anu Ramana
(74) *Attorney, Agent, or Firm* — Howard & Howard Attorneys PLLC (57) ABSTRACT

Systems and methods for treating a vertebral body. An intravertebral implant includes an anterior end element and a plate comprising a planar bearing surface. The plate may be exactly two plates movable in only a cranio-caudal expansion plane. A pedicle fixation is coupled to the intravertebral implant and includes a hollow sleeve. The pedicle fixation is configured to be secured to the pedicle to control an insertion depth of the intravertebral implant within the vertebral body. A central traction member is movably disposed within the hollow sleeve of the pedicle fixation to
(Continued)

deploy the planar bearing surface(s). The central traction member may be rotatable within the hollow sleeve. An expansion instrument may move the central traction member relative to the pedicle fixation. The intravertebral implant may be locked relative to the pedicle fixation in six degrees of freedom.

15 Claims, 8 Drawing Sheets

Related U.S. Application Data continuation of application No. 15/107,886, filed as application No. PCT/FR2014/053549 on Dec. 23, 2014, now Pat. No. 10,603,080.

(51) Int. Cl.
A61B 17/88 (2006.01)
A61F 2/44 (2006.01)
A61F 2/46 (2006.01)

(52) U.S. Cl.
CPC ............ *A61B 17/8858* (2013.01); *A61F 2/44* (2013.01); *A61F 2/4611* (2013.01); *A61F 2220/0016* (2013.01)

(56) References Cited

U.S. PATENT DOCUMENTS

| | | | |
|---|---|---|---|
| 4,961,740 | A | 10/1990 | Ray et al. |
| 4,969,888 | A | 11/1990 | Scholten et al. |
| 5,059,193 | A | 10/1991 | Kuslich |
| 5,108,404 | A | 4/1992 | Scholten et al. |
| 5,113,846 | A * | 5/1992 | Hiltebrandt ........ A61B 17/0218 604/105 |
| 5,209,753 | A | 5/1993 | Biedermann et al. |
| 5,454,365 | A * | 10/1995 | Bonutti ............. A61B 17/0218 606/198 |
| 5,649,902 | A | 7/1997 | Yoon |
| 5,665,122 | A | 9/1997 | Kambin |
| 5,693,100 | A | 12/1997 | Pisharodi |
| 5,695,515 | A | 12/1997 | Orejola |
| 5,704,860 | A | 1/1998 | Stief |
| 5,713,907 | A | 2/1998 | Hogendijk et al. |
| 5,720,746 | A | 2/1998 | Soubeiran |
| 5,749,916 | A | 5/1998 | Richelsoph |
| 5,800,500 | A | 9/1998 | Spelman et al. |
| 5,800,550 | A | 9/1998 | Sertich |
| 5,908,448 | A | 6/1999 | Roberts et al. |
| 5,972,015 | A | 10/1999 | Scribner et al. |
| 5,980,522 | A | 11/1999 | Koros et al. |
| 6,039,761 | A | 3/2000 | Li et al. |
| 6,066,154 | A | 5/2000 | Reiley et al. |
| 6,102,950 | A | 8/2000 | Vaccaro |
| 6,126,689 | A | 10/2000 | Brett |
| 6,127,597 | A | 10/2000 | Beyar et al. |
| 6,176,882 | B1 | 1/2001 | Biedermann et al. |
| 6,183,517 | B1 | 2/2001 | Suddaby |
| 6,190,414 | B1 | 2/2001 | Young et al. |
| 6,193,757 | B1 | 2/2001 | Foley et al. |
| 6,197,033 | B1 | 3/2001 | Haid, Jr. et al. |
| 6,214,050 | B1 | 4/2001 | Huene |
| 6,235,043 | B1 | 5/2001 | Reiley et al. |
| 6,248,110 | B1 | 6/2001 | Reiley et al. |
| 6,261,289 | B1 | 7/2001 | Levy |
| 6,280,456 | B1 | 8/2001 | Scribner et al. |
| 6,332,895 | B1 | 12/2001 | Suddaby |
| 6,395,031 | B1 | 5/2002 | Foley et al. |
| 6,423,083 | B2 | 7/2002 | Reiley et al. |
| 6,454,807 | B1 | 9/2002 | Jackson |
| 6,488,710 | B2 | 12/2002 | Besselink |
| 6,554,833 | B2 | 4/2003 | Levy et al. |
| 6,582,431 | B1 | 6/2003 | Ray |
| 6,595,998 | B2 | 7/2003 | Johnson et al. |
| 6,607,544 | B1 | 8/2003 | Boucher et al. |
| 6,623,505 | B2 | 9/2003 | Scribner et al. |
| 6,632,235 | B2 | 10/2003 | Weikel et al. |
| 6,663,647 | B2 | 12/2003 | Reiley et al. |
| 6,664,897 | B2 | 12/2003 | Pape et al. |
| 6,676,665 | B2 | 1/2004 | Foley et al. |
| 6,716,216 | B1 | 4/2004 | Boucher et al. |
| 6,719,773 | B1 | 4/2004 | Boucher et al. |
| 6,726,691 | B2 | 4/2004 | Osorio et al. |
| 6,730,126 | B2 | 5/2004 | Boehm, Jr. et al. |
| 6,740,093 | B2 | 5/2004 | Hochschuler et al. |
| 6,749,595 | B1 | 6/2004 | Murphy |
| 6,783,530 | B1 | 8/2004 | Levy |
| 6,929,647 | B2 | 8/2005 | Cohen |
| 6,953,477 | B2 | 10/2005 | Berry |
| 6,979,341 | B2 | 12/2005 | Scribner et al. |
| 6,981,981 | B2 | 1/2006 | Reiley et al. |
| 7,044,954 | B2 | 5/2006 | Reiley et al. |
| 7,070,598 | B2 | 7/2006 | Lim et al. |
| 7,083,650 | B2 | 8/2006 | Moskowitz et al. |
| 7,087,055 | B2 | 8/2006 | Lim et al. |
| 7,153,306 | B2 | 12/2006 | Ralph et al. |
| 7,217,293 | B2 | 5/2007 | Branch, Jr. |
| 7,226,481 | B2 | 6/2007 | Kuslich |
| 7,234,468 | B2 | 6/2007 | Johnson et al. |
| 7,241,303 | B2 | 7/2007 | Reiss et al. |
| 7,261,720 | B2 | 8/2007 | Stevens et al. |
| 7,264,622 | B2 | 9/2007 | Michelson |
| 7,291,150 | B2 | 11/2007 | Graf |
| 7,318,839 | B2 | 1/2008 | Malberg et al. |
| 7,507,241 | B2 | 3/2009 | Levy et al. |
| 7,513,900 | B2 | 4/2009 | Carrison et al. |
| 7,591,822 | B2 | 9/2009 | Olson, Jr. et al. |
| 7,621,950 | B1 | 11/2009 | Globerman et al. |
| 7,625,377 | B2 | 12/2009 | Veldhuizen et al. |
| 7,727,279 | B2 | 6/2010 | Zipnick et al. |
| 7,744,637 | B2 | 6/2010 | Johnson et al. |
| 7,749,255 | B2 | 7/2010 | Johnson et al. |
| 7,758,644 | B2 | 7/2010 | Trieu |
| 7,763,028 | B2 | 7/2010 | Lim et al. |
| 7,763,074 | B2 | 7/2010 | Altarac et al. |
| 7,799,080 | B2 | 9/2010 | Doty |
| 7,846,206 | B2 | 12/2010 | Oglaza et al. |
| 7,879,104 | B2 | 2/2011 | Dewey et al. |
| 7,901,409 | B2 | 3/2011 | Canaveral et al. |
| 7,905,885 | B2 | 3/2011 | Johnson et al. |
| 7,909,825 | B2 * | 3/2011 | Saravia ............. A61B 17/7266 606/66 |
| 8,062,336 | B2 * | 11/2011 | Triplett ................. A61B 17/70 606/313 |
| 8,133,232 | B2 | 3/2012 | Levy et al. |
| 8,152,813 | B2 | 4/2012 | Osorio et al. |
| 8,236,058 | B2 | 8/2012 | Fabian et al. |
| 8,282,520 | B2 | 10/2012 | Kurematsu et al. |
| 8,292,890 | B2 | 10/2012 | Wu |
| 8,317,802 | B1 | 11/2012 | Manzi et al. |
| 8,323,309 | B2 | 12/2012 | Khairkhahan et al. |
| 8,328,818 | B1 | 12/2012 | Seifert et al. |
| 8,372,115 | B2 | 2/2013 | Kohm et al. |
| 8,409,282 | B2 | 4/2013 | Kim |
| 8,425,559 | B2 | 4/2013 | Tebbe et al. |
| 8,491,591 | B2 | 7/2013 | Furderer |
| 8,628,577 | B1 | 1/2014 | Jimenez |
| 8,636,746 | B2 | 1/2014 | Jimenez et al. |
| 8,709,086 | B2 | 4/2014 | Glerum |
| 8,784,491 | B2 | 7/2014 | Biedermann et al. |
| 8,864,833 | B2 | 10/2014 | Glerum et al. |
| 8,888,853 | B2 | 11/2014 | Glerum et al. |
| 8,932,302 | B2 | 1/2015 | Jimenez et al. |
| 8,940,048 | B2 | 1/2015 | Butler et al. |
| 8,945,190 | B2 | 2/2015 | Culbert et al. |
| 8,961,609 | B2 | 2/2015 | Schaller |
| 8,986,386 | B2 * | 3/2015 | Oglaza ................. A61F 2/4611 606/90 |
| 8,998,923 | B2 | 4/2015 | Chirico et al. |
| 9,034,041 | B2 | 5/2015 | Wolters et al. |
| 9,173,747 | B2 | 11/2015 | Hansell et al. |
| 9,295,502 | B2 | 3/2016 | Fuerderer |

(56) References Cited

U.S. PATENT DOCUMENTS

| | | | |
|---|---|---|---|
| 9,326,806 B2 | 5/2016 | Lin et al. | |
| 9,408,707 B2 | 8/2016 | Oglaza et al. | |
| 9,439,770 B2 | 9/2016 | Biedermann et al. | |
| 9,445,856 B2 | 9/2016 | Seifert et al. | |
| 9,526,621 B2 | 12/2016 | Kuslich | |
| 9,579,130 B2* | 2/2017 | Oglaza | A61B 17/7065 |
| 10,603,080 B2 | 3/2020 | Oglaza et al. | |
| 2001/0032020 A1 | 10/2001 | Besselink | |
| 2002/0058947 A1 | 5/2002 | Hochschuler et al. | |
| 2002/0065548 A1 | 5/2002 | Birdsall et al. | |
| 2002/0068974 A1 | 6/2002 | Kuslich et al. | |
| 2002/0120327 A1 | 8/2002 | Cox et al. | |
| 2002/0143401 A1 | 10/2002 | Michelson | |
| 2002/0151976 A1 | 10/2002 | Foley et al. | |
| 2002/0198532 A1 | 12/2002 | Michelson | |
| 2003/0055427 A1* | 3/2003 | Graf | A61F 2/4405 |
| | | | 606/256 |
| 2003/0065396 A1 | 4/2003 | Michelson | |
| 2003/0074064 A1 | 4/2003 | Gerbec et al. | |
| 2003/0171812 A1 | 9/2003 | Grunberg et al. | |
| 2003/0220650 A1 | 11/2003 | Major et al. | |
| 2003/0236520 A1 | 12/2003 | Lim et al. | |
| 2004/0073308 A1 | 4/2004 | Kuslich et al. | |
| 2004/0087947 A1 | 5/2004 | Lim et al. | |
| 2004/0087994 A1 | 5/2004 | Suddaby | |
| 2004/0102774 A1 | 5/2004 | Trieu | |
| 2004/0133280 A1 | 7/2004 | Trieu | |
| 2004/0143827 A1 | 7/2004 | de Jong | |
| 2004/0167625 A1 | 8/2004 | Beyar et al. | |
| 2004/0210231 A1 | 10/2004 | Boucher et al. | |
| 2004/0215343 A1 | 10/2004 | Hochschuler et al. | |
| 2004/0236342 A1 | 11/2004 | Ferree et al. | |
| 2005/0107800 A1 | 5/2005 | Frankel et al. | |
| 2005/0143827 A1 | 6/2005 | Globerman et al. | |
| 2005/0182416 A1 | 8/2005 | Lim et al. | |
| 2005/0222681 A1 | 10/2005 | Richley et al. | |
| 2005/0228391 A1 | 10/2005 | Levy et al. | |
| 2005/0234493 A1 | 10/2005 | Carr et al. | |
| 2005/0261781 A1 | 11/2005 | Sennett et al. | |
| 2005/0273135 A1 | 12/2005 | Chanduszko et al. | |
| 2005/0278036 A1 | 12/2005 | Leonard et al. | |
| 2006/0004455 A1 | 1/2006 | Leonard et al. | |
| 2006/0085070 A1 | 4/2006 | Kim | |
| 2006/0116689 A1 | 6/2006 | Albans et al. | |
| 2006/0129101 A1 | 6/2006 | McGuckin | |
| 2006/0149268 A1 | 7/2006 | Truckai et al. | |
| 2006/0149379 A1 | 7/2006 | Kuslich et al. | |
| 2006/0184192 A1 | 8/2006 | Markworth et al. | |
| 2006/0235423 A1 | 10/2006 | Cantu | |
| 2006/0241644 A1 | 10/2006 | Osorio et al. | |
| 2006/0271049 A1 | 11/2006 | Zucherman et al. | |
| 2006/0281595 A1 | 12/2006 | Narita et al. | |
| 2007/0016303 A1 | 1/2007 | Jackson | |
| 2007/0021836 A1 | 1/2007 | Poty | |
| 2007/0032790 A1 | 2/2007 | Aschmann et al. | |
| 2007/0032791 A1 | 2/2007 | Greenhalgh | |
| 2007/0055201 A1 | 3/2007 | Seto et al. | |
| 2007/0093899 A1 | 4/2007 | Dutoit et al. | |
| 2007/0142915 A1 | 6/2007 | Altarac et al. | |
| 2007/0149978 A1 | 6/2007 | Shezifi et al. | |
| 2007/0173826 A1 | 7/2007 | Canaveral et al. | |
| 2007/0173832 A1 | 7/2007 | Tebbe et al. | |
| 2007/0173939 A1 | 7/2007 | Kim et al. | |
| 2007/0225705 A1 | 9/2007 | Osorio et al. | |
| 2007/0260315 A1 | 11/2007 | Foley et al. | |
| 2008/0051894 A1 | 2/2008 | Malandain et al. | |
| 2008/0058823 A1 | 3/2008 | Reiley et al. | |
| 2008/0065087 A1 | 3/2008 | Osorio et al. | |
| 2008/0065089 A1 | 3/2008 | Osorio et al. | |
| 2008/0086133 A1 | 4/2008 | Kuslich et al. | |
| 2008/0114367 A1 | 5/2008 | Meyer | |
| 2008/0125784 A1 | 5/2008 | Rabiner et al. | |
| 2008/0140079 A1 | 6/2008 | Osorio et al. | |
| 2008/0140207 A1 | 6/2008 | Olmos et al. | |
| 2008/0147193 A1 | 6/2008 | Matthis et al. | |
| 2008/0167657 A1 | 7/2008 | Greenhalgh | |
| 2008/0183204 A1 | 7/2008 | Greenhalgh et al. | |
| 2008/0269766 A1 | 10/2008 | Justis | |
| 2008/0280712 A1 | 11/2008 | Ryouno et al. | |
| 2009/0005782 A1 | 1/2009 | Chirico et al. | |
| 2009/0005821 A1 | 1/2009 | Chirico | |
| 2009/0171390 A1 | 7/2009 | Sankaran | |
| 2009/0228012 A1 | 9/2009 | Gangji et al. | |
| 2009/0234398 A1 | 9/2009 | Chirico et al. | |
| 2009/0264927 A1 | 10/2009 | Ginsberg et al. | |
| 2009/0276048 A1 | 11/2009 | Chirico et al. | |
| 2009/0281628 A1 | 11/2009 | Oglaza et al. | |
| 2009/0292323 A1 | 11/2009 | Chirico et al. | |
| 2009/0299378 A1 | 12/2009 | Knopp | |
| 2009/0306715 A1 | 12/2009 | Jackson et al. | |
| 2009/0326581 A1 | 12/2009 | Galley | |
| 2010/0069913 A1 | 3/2010 | Chirico et al. | |
| 2010/0070035 A1 | 3/2010 | Mayer | |
| 2010/0185291 A1 | 7/2010 | Jimenez et al. | |
| 2010/0324607 A1 | 12/2010 | Davis | |
| 2011/0021298 A1 | 1/2011 | Kurematsu et al. | |
| 2011/0032020 A1 | 2/2011 | Campbell et al. | |
| 2011/0046739 A1 | 2/2011 | Oglaza et al. | |
| 2011/0066186 A1 | 3/2011 | Boyer, II et al. | |
| 2011/0130232 A1 | 6/2011 | Barrette et al. | |
| 2012/0071977 A1 | 3/2012 | Oglaza et al. | |
| 2012/0123481 A1 | 5/2012 | Lin | |
| 2012/0150228 A1 | 6/2012 | Zappacosta et al. | |
| 2014/0031940 A1 | 1/2014 | Banouskou | |
| 2014/0114368 A1 | 4/2014 | Lin et al. | |
| 2014/0135780 A1 | 5/2014 | Lee et al. | |
| 2015/0250518 A1 | 9/2015 | Chirico et al. | |
| 2016/0157898 A1 | 6/2016 | Fuerderer | |
| 2017/0000622 A1 | 1/2017 | Thommen et al. | |
| 2020/0187992 A1 | 6/2020 | Oglaza et al. | |

FOREIGN PATENT DOCUMENTS

| | | |
|---|---|---|
| CN | 1713863 A | 12/2005 |
| CN | 1830399 A | 9/2006 |
| CN | 101031259 A | 9/2007 |
| CN | 101530343 A | 9/2009 |
| CN | 102427769 A | 4/2012 |
| DE | 20017962 U1 | 1/2001 |
| DE | 20303642 U1 | 4/2003 |
| EP | 0567424 A1 | 10/1993 |
| EP | 0571555 A1 | 12/1993 |
| EP | 0796593 A2 | 9/1997 |
| EP | 1778136 A2 | 5/2007 |
| EP | 2074956 A1 | 7/2009 |
| FR | 2782632 A1 | 3/2000 |
| FR | 2796268 A1 | 1/2001 |
| GB | 2435292 A | 8/2007 |
| GB | 2436292 A | 9/2007 |
| JP | S62054313 A | 3/1987 |
| JP | 2000070274 A | 3/2000 |
| JP | 2001173863 A | 6/2001 |
| JP | 2002535066 A | 10/2002 |
| JP | 2006507090 A | 3/2006 |
| JP | 2008501462 A | 1/2008 |
| KR | 20070068338 A | 6/2007 |
| RU | 2070006 C1 | 12/1996 |
| WO | 9834568 A1 | 8/1998 |
| WO | 9902214 A1 | 1/1999 |
| WO | 1999021501 A1 | 5/1999 |
| WO | 9952447 A1 | 10/1999 |
| WO | 0044319 A1 | 8/2000 |
| WO | 0049978 A1 | 8/2000 |
| WO | 0078253 A1 | 12/2000 |
| WO | 0101895 A1 | 1/2001 |
| WO | 01060263 A1 | 8/2001 |
| WO | 200154598 A1 | 8/2001 |
| WO | 0166047 A1 | 9/2001 |
| WO | 200176492 A1 | 10/2001 |
| WO | 0230338 A1 | 4/2002 |
| WO | 03003951 A1 | 1/2003 |
| WO | 2004000166 A2 | 12/2003 |
| WO | 2004019756 A2 | 3/2004 |
| WO | 2004034924 A3 | 6/2004 |

(56) References Cited

FOREIGN PATENT DOCUMENTS

| | | |
|---|---|---|
| WO | 2004047689 A1 | 6/2004 |
| WO | 2004026188 A3 | 10/2004 |
| WO | 2004086934 A3 | 11/2004 |
| WO | 2005048856 A1 | 6/2005 |
| WO | 2005120400 A3 | 4/2006 |
| WO | 2006042206 A2 | 4/2006 |
| WO | 2006068682 A1 | 6/2006 |
| WO | 2006116760 A2 | 11/2006 |
| WO | 2007075788 A2 | 7/2007 |
| WO | 2007076308 A2 | 7/2007 |
| WO | 2007079237 A2 | 7/2007 |
| WO | 2007084239 A2 | 7/2007 |
| WO | 2007076374 A3 | 12/2007 |
| WO | 2007073488 A3 | 4/2008 |
| WO | 2007041665 A3 | 7/2008 |
| WO | 2007076376 A3 | 12/2008 |
| WO | 2009005851 A1 | 1/2009 |
| WO | 2009037509 A1 | 3/2009 |
| WO | 2009100200 A1 | 8/2009 |
| WO | 2009125243 A1 | 10/2009 |
| WO | 2010100287 A1 | 9/2010 |
| WO | 2010103344 A1 | 9/2010 |
| WO | 2022025759 A1 | 2/2022 |

OTHER PUBLICATIONS

Chinese Search Report for Application 201480070702.5 dated Feb. 2, 2018.
European Search Report dated Feb. 22, 2013 for EP Application No. 12191848.6, filed Jun. 8, 2005.
French Preliminary Search Report corresponding to French Patent Application No. 0406211 dated Feb. 15, 2005.
French Preliminary Search Report for Application No. FR1363467 dated Sep. 24, 2014.
International Preliminary Report on Patentability dated Dec. 14, 2006 for PCT/IB2005/002631, filed Jun. 8, 2005.
International Preliminary Report on Patentability dated Oct. 12, 2010 for PCT/IB2008/002246, filed Apr. 8, 2008.
International Preliminary Report on Patentability dated Oct. 8, 2013 for PCT/IB2011/001480, filed Apr. 7, 2011.
International Preliminary Report on Patentability, dated Sep. 13, 2011 for PCT/IB2009/005385, filed Mar. 12, 2009.
International Search Report and Written Opinion of the International Searching Authority corresponding to International PCT/IB2005/002631 dated Feb. 7, 2006.
International Search Report and Written Opinion, dated Feb. 25, 2015 for International Application No. PCT/FR2014/053549, filed Dec. 23, 2014, and English translations of the International Search Report and Written Opinion.
International Search Report corresponding to International PCT/IB2008/002246 dated Jan. 29, 2009.
International Search Report dated Dec. 12, 2009 and Written Opinion for PCT/IB2009/005385, filed Mar. 12, 2009.
International Search Report dated Dec. 6, 2011 for PCT/IB2011/001480, filed Apr. 7, 2011.
International Search Report for Application No. PCT/US2009/033192 dated Mar. 19, 2009.
Kuslich et al., U.S. Appl. No. 60/219,853, filed Jul. 21, 2000, titled "Expandable porous mesh bag device for reduction, filling,fixation and supporting of bone".
Russian Search Report for RU2011141272 dated Feb. 8, 2013.

* cited by examiner

FIG. 10B ated with the pedicle fixation element,
making it possible to adjoin to the expandable intravertebral
implant means completing the bone correction, for example
using posterior rods or other system intended to stabilise the
fracture site further.

SYSTEM INCLUDING AN INTRAVERTEBRAL IMPLANT AND A PEDICLE FIXATION FOR TREATING A VERTEBRAL BODY

PRIORITY CLAIM

This is a continuation application of co-pending U.S. patent application Ser. No. 16/801,842, filed Feb. 26, 2020, which is a continuation of U.S. patent application Ser. No. 15/107,886, filed Jun. 23, 2016, now U.S. Pat. No. 10,603,080, which is a national stage entry of International Application No. PCT/FR2014/053549, filed Dec. 23, 2014, which claims priority to and all the benefits of French Patent Application No. 1363467, filed Dec. 23, 2013. The entire contents of each of the above applications are hereby incorporated by reference.

FIELD OF THE INVENTION

The present invention relates to an expandable intravertebral implant system with posterior pedicle fixation. More particularly, the present invention relates to an expandable intravertebral implant system offering enhanced vertebral anchoring by adding a pedicle dowel firmly anchored in a vertebral pedicle.

STATE OF THE RELATED ART

Several vertebroplasty techniques are known for performing vertebral correction enabling a vertebra deformed following bone compression, for example due to osteoporosis or an injury, to return to the initial shape or morphology thereof.

For example, the kyphoplasty technique is known, consisting of introducing an inflatable balloon into a vertebra, then sending a pressurized fluid into the balloon placed in the vertebra in order to force the cortical envelope of the vertebra, and particularly the lower and upper vertebral plates to return to a corrected shape under the effect of the pressure. Once the cortical bone envelope has been corrected, the balloon is then deflated, and removed from the vertebra, in order to be able to inject therein a bone cement intended to give the corrected vertebra a stable mechanical strength over time.

Through the international patent application WO2005/120400 in particular, an expandable implant is known, comprising a first and a second opposite plates, suitable for respectively forming a first and a second bearing surfaces in a vertebral body; these two bearing surfaces being called upon to separate from one another along a predefined expansion plane. The expandable implant is positioned in the vertebral body, and the plates are deployed along an expansion plane which corresponds to the bone correction plane sought. A bone cement is then injected in order to stabilise the bone correction.

The bone cement may be injected with a relatively low pressure by means of the implant which remains in position in the vertebral body.

In the case of the most severe injuries, the use of the methods cited above may prove to be insufficient. The repair of vertebral fractures, and particularly vertebral fractures induced by compression is then preferentially performed by means of screws inserted into the pedicles of the over- and underlying vertebrae of the compressed vertebra, these screws being associated with posterior rods, thus mechanically connecting the two over- and underlying vertebrae to enable vertebral consolidation. Pedicle screws are well-known in the prior art. Screws such as those described in the U.S. Pat. No. 5,209,753 are particularly known.

The drawback of this technique lies in the fusion of two vertebral joint levels caused by the fixation of the posterior rods connecting the over- and underlying vertebrae. Furthermore, these methods do not always enable bone correction of the compressed vertebra but merely the stabilisation of three adjacent vertebrae and thus the locking of two joint levels. The surgical act associated with this procedure is furthermore very invasive and requires access to at least two vertebrae.

In order to remedy these drawbacks, it appears to be necessary to provide a device enabling the repair of vertebral fractures, and particularly severe vertebral fractures caused by compression, preventing fusion and enabling consolidation, at the pedicle, of an expandable intravertebral implant situated in the vertebral body.

As such, the aim of the invention is to associate with an expandable intravertebral implant, positioned in a vertebral body, a pedicle fixation (for example dowel or sleeve), intended to be anchored in the pedicle. This pedicle fixation ensures high-quality support and anchoring of the bone. Indeed, while the vertebral body consists of spongy bone, having a high porosity of 30 to 90%, the pedicle consists of cortical bone, having a porosity of 5 to 30%, thus offering strong mechanical support for the intravertebral implant and making it possible to reconstruct vertebral fractures, and particularly vertebral fractures caused by compression, even the most severe.

Extendable bone implant systems comprising an additional anchoring in the pedicle bone are known, such as for example the systems described in the patent applications EP 2 074 956 and US 2009/005821. However, these systems describe an expandable member rigidly connected to said pedicle fixation, for example by screwing both parts. For this reason, the direction of expansion of the expandable member and the positioning of the member in the vertebral body are directly dependent on the position of the pedicle fixation.

The invention has the advantage of enabling the deployment of the expandable intravertebral implant independently, along at least one degree of freedom, of the position of the pedicle fixation. The implant system also makes it possible to secure (i.e. lock all the degrees of freedom) said extendable intravertebral implant with respect to the pedicle fixation, when the implant system is positioned in extension in the vertebra.

Advantageously, a posterior element acting as a connection system is associated with the pedicle fixation element, making it possible to adjoin to the expandable intravertebral implant means completing the bone correction, for example using posterior rods or other system intended to stabilise the fracture site further.

As such, the present invention ensures vertebral correction using a modular expandable intravertebral implant system with posterior pedicle fixation.

SUMMARY

The invention thus relates to an expandable intravertebral implant system comprising an intravertebral implant comprising an expandable anterior part in a vertebral body and a posterior part; and a pedicle fixation having at least one hollow portion for receiving the posterior part of the intravertebral implant.

According to one embodiment, the pedicle fixation comprises an external thread ensuring the anchoring of said pedicle fixation in a vertebral pedicle.

According to one embodiment, the pedicle fixation comprises a hollow posterior inner portion and a hollow anterior inner portion wherein the posterior part of the intravertebral implant can move along at least one degree of freedom.

According to one embodiment, the pedicle fixation comprises a main axis and the posterior part of the intravertebral implant can move in translation and in rotation, along the main axis of the pedicle fixation, in the anterior inner portion of the pedicle fixation; in such a way that the direction of expansion of the anterior part of the anterior part of the intravertebral implant is independent from the position of the pedicle fixation in the vertebral pedicle.

According to one embodiment, the anterior part of the intravertebral implant comprises a first and a second plates, suitable for respectively forming a first and a second bearing surfaces in a vertebral body; these two surfaces being suitable for being separated from one another along a predefined expansion plane.

According to one embodiment, the anterior inner portion comprises at least one groove on the inner surface thereof.

According to one embodiment, a posterior portion of the posterior part of the intravertebral implant comprises a cylindrical recess and at least one securing means suitable for locking in rotation and in translation the relative movements between the intravertebral implant and the pedicle fixation.

According to one embodiment, the securing means comprises at least one through hole, passing through the posterior portion and a peripheral chamber to the surface of the posterior portion in fluid communication with the at least one through hole.

According to one embodiment, the securing means comprises at least two slots extending axially along the posterior portion, an internal thread and a flared posterior end; suitable for engaging with a conical expansion cap.

According to one embodiment, the posterior element is secured to the pedicle fixation by means of a threaded rod screwed into an internal thread of the posterior inner portion.

According to one embodiment, the posterior element comprises a posterior portion suitable for assembly with additional posterior fixation elements such as rods or artificial ligaments.

BRIEF DESCRIPTION OF THE FIGURES

Further specific features and advantages will emerge clearly from the description hereinafter, by way of indication and in no way limiting, with reference to the appended drawings, wherein.

The drawings in the figures are not to scale. Obviously, the scope of the invention is not restricted to examples of embodiments more specifically described and represented with reference to the appended figures; on the contrary, it includes any alternative embodiments.

REFERENCES

1 Anterior part of the intravertebral implant,
11 Posterior part of the intravertebral implant,
121 Shoulder,
122 Cylindrical recess,
123 Chamber,
124 Through hole,
125 Slot,
126 Internal thread,
127 Flared posterior end,
128 Posterior portion of the posterior part of the intravertebral implant,
13 Central traction tube,
131 Through hole,
2 Pedicle fixation, particularly pedicle dowel,
21 External thread,
22 Posterior inner portion, 221 Internal thread,
23 Anterior inner portion,
231 Groove,
24 Means for rotating the pedicle fixation—Notch,
25 Entry chamfer,
3 Posterior element,
31 Anterior portion,
311 External thread,
32 Posterior portion,
33 Bearing surface,
4 Vertebra,
5 Insertion instrument,
51 Cannula rotatably connected to the pedicle fixation,
52 Expansion tube,
6 Conical expansion cap.

DETAILED DESCRIPTION

The present invention relates to an expandable intravertebral implant system with posterior pedicle fixation.

According to a first embodiment, the implant system comprises an intravertebral implant associated with a pedicle fixation ensuring additional anchoring at the vertebral pedicle.

Figure 1:
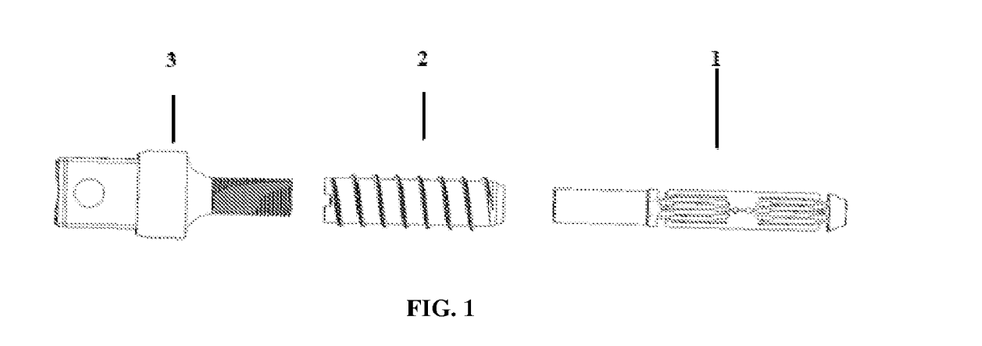
FIG. 1 is an exploded view of the implant system according to one embodiment of the present invention.

According to a second embodiment, as represent in FIG. 1, the implant system comprises an intravertebral implant 1 associated with a pedicle fixation 2 and with a posterior element 3 suitable for connecting, posterior to the vertebra, any device intended to stabilise, reinforce or repair the vertebral fracture, particularly the vertebral fracture caused by compression.

Intravertebral Implant

Figure 2:
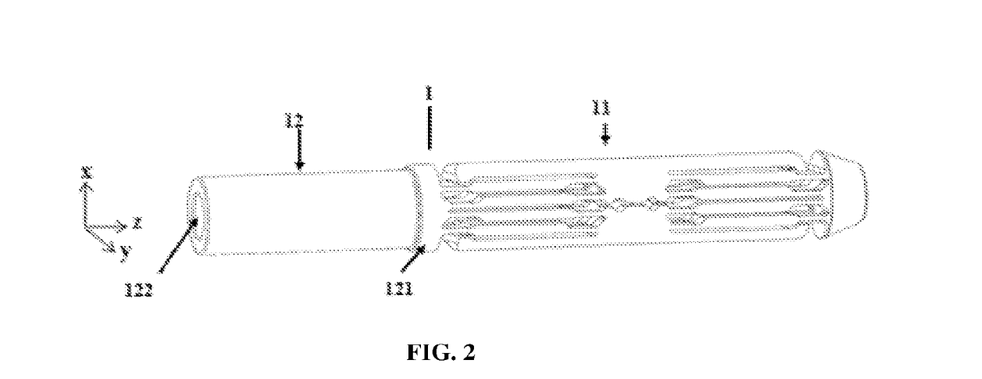
FIG. 2 is a side view of the intravertebral implant according to one embodiment of the present invention.

As represented in FIG. 2, the intravertebral implant 1 according to the present invention comprises an anterior part 11 and a posterior part 12.

According to one embodiment, the anterior part 11 corresponds to a deformable and expandable intravertebral implant 1 such as the SpineJack® implant marketed by the company VEXIM, known to those skilled in the art and also described in the patent application EP 1 778 136, incorporated herein by reference. It is specified that those skilled in the art, on reading said patent application, would readily find the features required for the embodiment of the present invention. In particular, the anterior part 11 of the intravertebral implant 1 of the present invention consists of an expandable part enabling bone correction and comprising:
   a predetermined single expansion plane, intrinsic to said anterior part 11,
   a first and a second opposite plates, suitable for respectively forming a first and a second bearing surfaces in a vertebral body; these two bearing surfaces being intended to separate from one another along said expansion plane upon expansion of the implant,
   a first and a second supports for each of said first and second plates, situated respectively thereunder, and
   means for setting a predetermined expansion value, including a veil of material arranged between said support and a corresponding plate, said veil having a predetermined thickness making it possible to monitor the expansion of the implant. According to one embodiment, said anterior part 11 also comprises a central traction tube 13 suitable for controlling the expansion of the first and second plates. According to one alternative embodiment, the anterior part 11 of the intravertebral implant 1 corresponds to any intravertebral implant known to those skilled in the art which is deformable, expandable and suitable for remaining in the vertebral body after expansion.

According to one embodiment, as represented in FIGS. 7A-B, 8A-B, 9A-B and 10A-B, the central traction tube 13 is hollow and comprises at least one through hole 131 suitable for injecting a filling material into the vertebra 4, such as bone cement, after the expansion of the first and second plates. According to one embodiment, the central traction tube 13 comprises at least 1, 2, 3, 4, 5, 6, 7, 8, 9, 10 through holes 131. According to one embodiment, the through hole(s) 131 pass(es) radially through the central traction tube 13 so as to enable fluid communication between the inner conduit and the outer surface. According to one embodiment, the central traction tube 13 comprises a plurality of through holes 131 regularly distributed on the surface thereof. According to one embodiment, the at least one through hole 131 is situated between the two plates so as to be in fluid communication with the inside of the vertebra after the expansion of the implant and the separation of the two plates. Advantageously, the injection of a filling material into the vertebra 4 makes it possible to hold the anterior part 11 of the implant 1 in position in the vertebral body after expansion. According to one embodiment, the filling material is a biocompatible bone cement, for example an ionic cement, a phosphocalcium cement, an acrylic cement or a composite thereof, or a resin. According to one embodiment, the filling material solidifies after injection. Advantageously, the solidification of the filling material makes it possible to consolidate the vertebra 4 and reinforce the strength of the implantation of the implant system in the vertebra 4.

According to one embodiment, the posterior part 12 is a hollow cylindrical body connected, at the anterior end thereof, to the posterior end of the anterior part 11 by a shoulder 121. Said posterior part 12 comprises a cylindrical recess 122 through which a central traction tube 13, initially situated in the anterior part 11, can slide. By pulling on the central traction tube 13, the central traction tube 13 slides in the cylindrical recess 122 of the posterior part 12 and the anterior and posterior ends of the anterior part 11 move closer, causing the expansion of the first and second plates of the anterior part 11 of the intravertebral implant 1. The central traction tube 13 is suitable for controlling the deployment of the expandable deformable anterior part 11. Once the traction tube 13 has been pulled inside the recess 122, the tube can no longer return to the initial position thereof, which holds the expansion of the anterior part 11, pending the injection of bone cement or substitute.

Figure 8A:
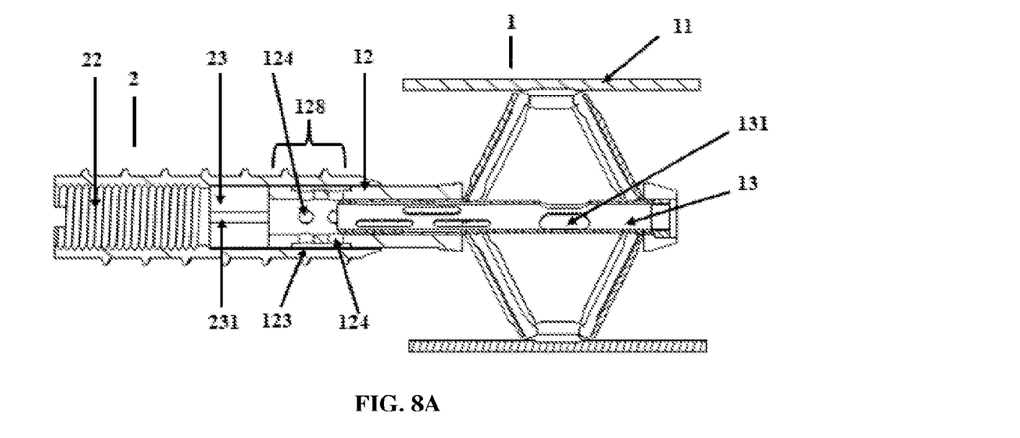
FIG. 8A is a sectional view of the implant system, after expansion of the anterior part of the implant illustrating the means for securing the pedicle fixation to the intravertebral implant according to one embodiment of the present invention.
Figure 8B:
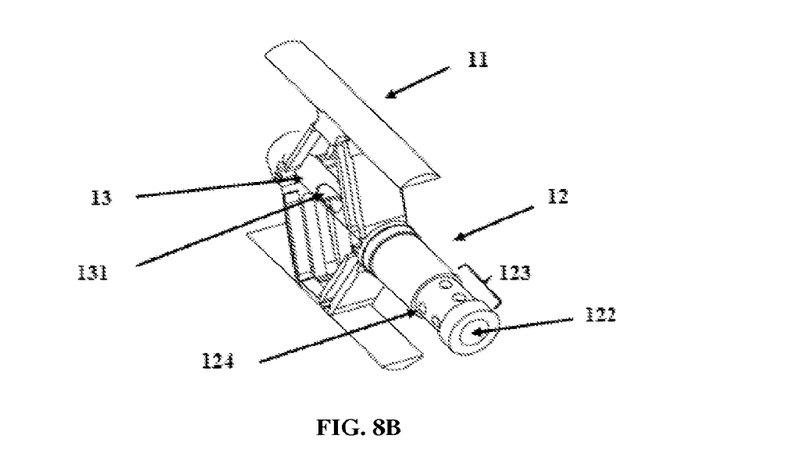
FIG. 8B is a perspective view of the intravertebral implant, after expansion of the anterior part of the implant illustrating the means for securing the pedicle fixation to the implant according to one embodiment of the present invention.

According to one embodiment illustrated in particular by FIG. 8B, the posterior part 12 of the intravertebral implant 1 comprises a cylindrical recess 122 and at least one through hole 124. Advantageously, the at least one through hole is situated in the posterior portion 128 of the posterior part 12. According to one embodiment, the posterior portion 128 corresponds to the portion of the posterior part 12 of the intravertebral implant 1 which remains permanently inside the anterior inner portion 23. According to one embodiment, the cylindrical recess 122 passes through the entire posterior part 12 of the implant 1. According to one embodiment, the posterior part 12 of the intravertebral implant 1, and particularly the posterior portion 128 further comprises a portion with a reduced outer diameter thus defining a peripheral chamber 123. According to one embodiment, the at least one through hole 124 passes through the posterior part 12 of the implant 1 from the cylindrical recess 122 to the peripheral chamber 123. According to one embodiment, the posterior part 12 of the implant, and particularly the posterior portion 128 thereof comprises at least 1, 2, 3, 4, 5, 6, 7, 8, 9, 10 through holes 124. According to one embodiment, the through holes 124 are regularly distributed on the posterior portion 128.

Figure 9A:
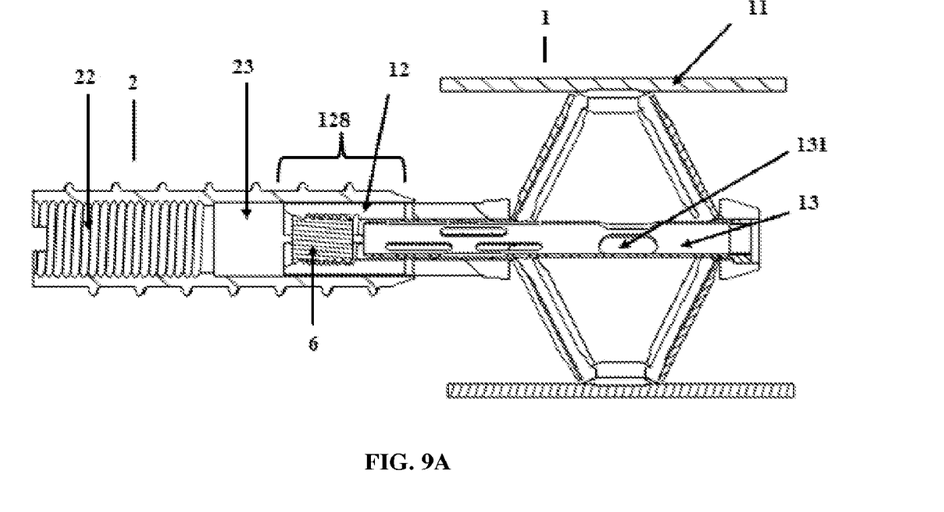
FIG. 9A is a sectional view of the implant system, after expansion of the anterior part of the implant illustrating the means for securing the pedicle fixation to the intravertebral implant according to one embodiment of the present invention.
Figure 9B:
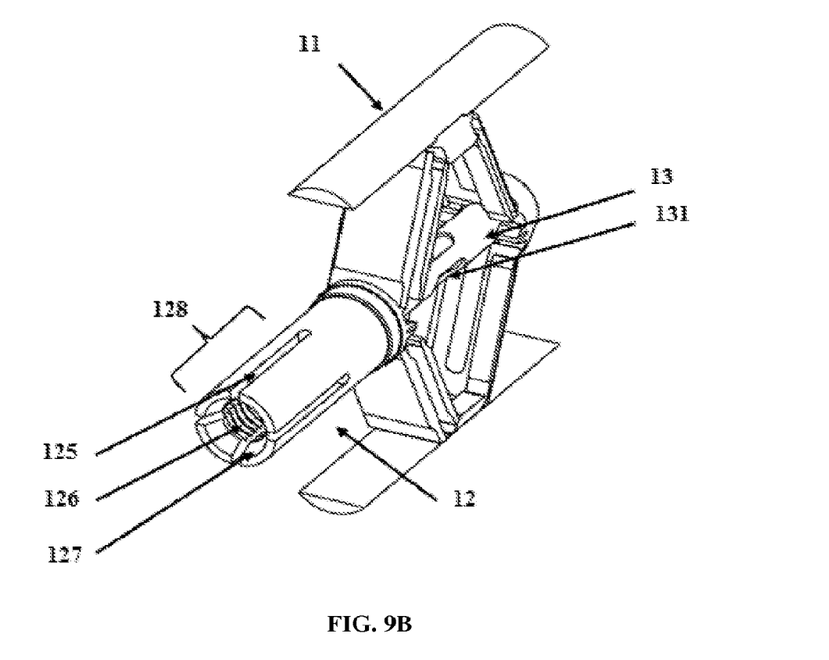
FIG. 9B is a perspective view of the implant system, after expansion of the anterior part of the implant illustrating the means for securing the pedicle fixation to the intravertebral implant according to one embodiment of the present invention.
Figure 10A:
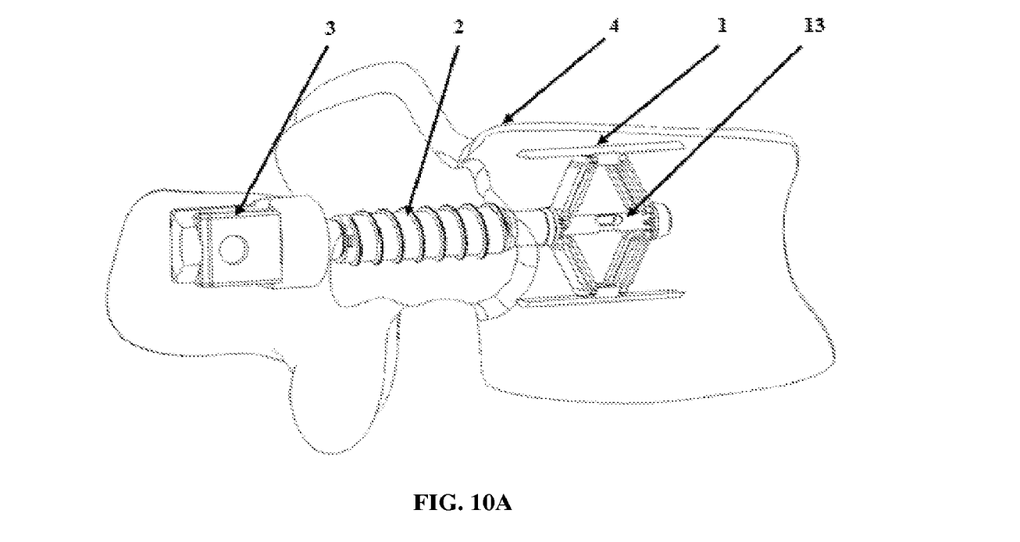
FIG. 10A is a side view of the implant system according to one embodiment of the present invention placed in a vertebra; said vertebra being represented as transparent, visible merely by the outlines thereof.
Figure 10B:
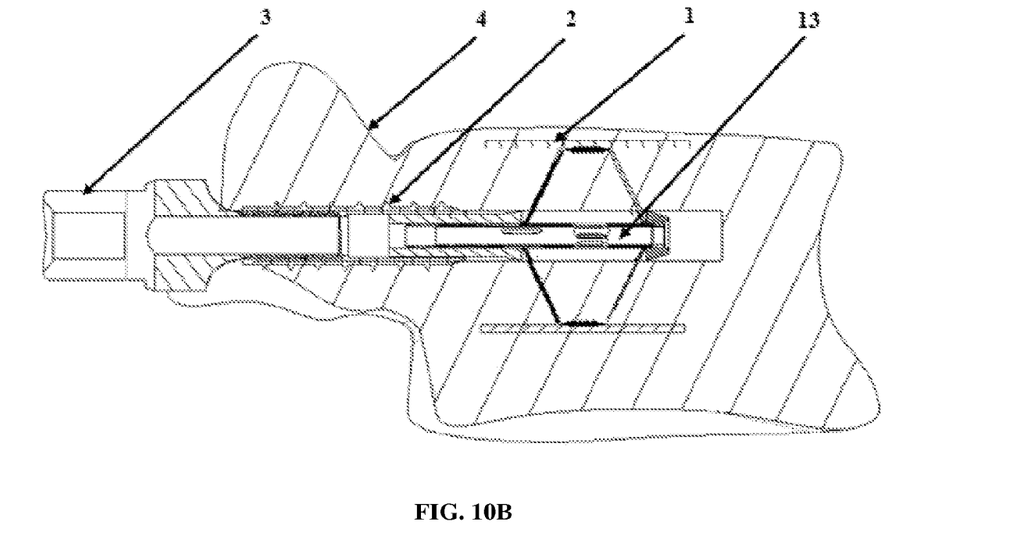
FIG. 10B is a sectional view of the implant system according to one embodiment of the present invention placed in a vertebra; said vertebra being represented as transparent, visible merely by the outlines thereof.

According to one embodiment illustrated by FIG. 9B, the posterior part 12 of the intravertebral implant 1 comprises a cylindrical recess 122 and at least one slot 125 through the posterior part 12 and extending axially. Advantageously, the at least one slot 125 is situated in the posterior portion 128 of the posterior part 12. According to one embodiment, the posterior portion 128 corresponds to the portion of the posterior part 12 of the intravertebral implant 1 which remains permanently inside the anterior inner portion 23. According to one embodiment, the cylindrical recess 122 passes through the entire posterior part 12 of the implant 1. According to one embodiment, the posterior part 12 of the intravertebral implant 1, and particularly the posterior portion 128 further comprises an internal thread 126 situated on the inner surface of the cylindrical recess 122. According to one embodiment, the posterior part 12 of the intravertebral implant 1, and particularly the posterior portion 128 further comprises a flared posterior end 127 suitable for engaging with a conical expansion cap 6. According to one embodiment, the posterior part 12 comprises at least 1, 2, 3, 4, 5, 6, 7, 8, 9, 10 slots 125. According to one embodiment, the slot 125 extends along all or part of the posterior portion 128. According to one embodiment, the thread 126 extends along all or part of the posterior portion 128.

According to one embodiment, the expansion of the intravertebral implant 1 is not due to the injection of a product into the posterior part of the implant 1. However, the injection of a filling material can make it possible to stabilise the implant once in the expansion position thereof. According to one embodiment, the intravertebral implant 1 does not comprise a pouch intended to be filled with a product (e.g. a filling material) so as to enable the expansion of the pouch. According to one embodiment, the injection of a filling material through the anterior part 11 alone, does not allow the expansion of the intravertebral implant 1.

According to one embodiment, the posterior part 12 of the intravertebral implant 1 does not comprise an outer thread intended to be screwed with the pedicle fixation 2.

Pedicle Fixation

Figure 3A:
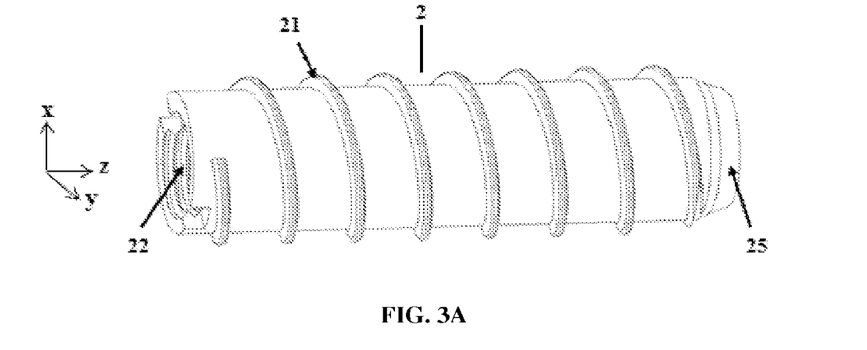
FIG. 3A is a side view of the pedicle fixation according to one embodiment of the present invention.
Figure 3B:
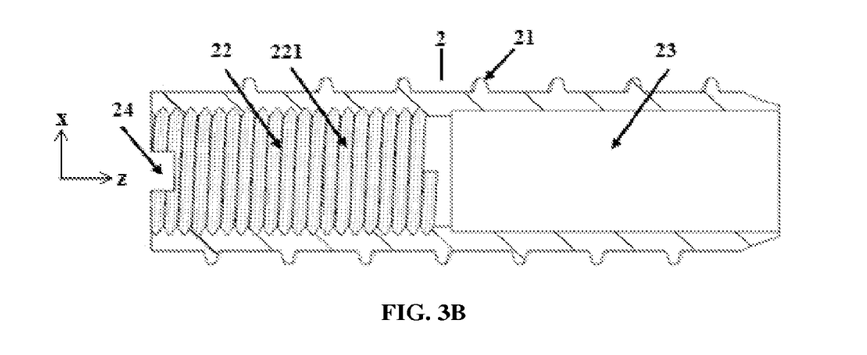
FIG. 3B is a sectional view of the pedicle fixation according to one embodiment of the present invention.

As represented in FIG. 3A, the pedicle fixation 2 according to the present invention comprises at least one thread 21. According to one embodiment, the pedicle fixation 2 comprises a thread 21 on the outer surface of the pedicle fixation 2. Said external thread 21 is suitable for providing bone anchoring in the pedicle. The anchoring of the pedicle fixation 2 in a vertebral pedicle offers additional mechanical support to the intravertebral implant 1, and particularly to the expandable anterior part 11 of said implant 1. The insertion of the pedicle fixation 2 in the bone tissue is facilitated by a chamfer 25 situated at the anterior end of the pedicle fixation 2. According to one embodiment, the outer surface of the pedicle fixation 2 has no texture other than that induced by an external thread, such as for example a meshed, striated or mottled structure. As represented in FIG. 3B, the pedicle fixation 2 is a hollow cylindrical pedicle dowel or sleeve comprising a posterior inner portion 22 and an anterior inner portion 23. According to one embodiment, the pedicle fixation 2 is not a solid pedicle screw comprising a hollow inner partial portion. According to one embodiment, the pedicle fixation 2 is hollow along the entire length thereof. According to one embodiment, the posterior and anterior inner portions 22, 23 do not have the same surface condition.

According to one embodiment, the posterior inner portion 22 comprises an internal thread 221 or any other means within the scope of those skilled in the art for connecting the fixation 2 to a posterior element 3.

According to one embodiment, the anterior inner portion 23 comprises a bore defining a hollow portion for receiving the posterior part 12 of the intravertebral implant 1. According to one embodiment, the surface of the anterior inner portion 23 is smooth. According to one embodiment, the surface of the anterior inner portion 23 is not threaded. According to one embodiment, the intravertebral implant 1, and particularly the posterior part 12, does not pass through the entire hollow pedicle fixation 2. According to one embodiment, the posterior part 12 of the intravertebral implant 1 is intended to be inserted inside the anterior inner portion 23. According to one embodiment, the posterior part 12 acts as a guide for the pedicle fixation 2. The shoulder 121 thus acts as a guiding stop for the fixation 2. According to one embodiment, the posterior part 12 of the intravertebral implant 1 can move along at least one degree of freedom, preferentially 2 degrees of freedom in the anterior inner portion 23 of the pedicle fixation 2. According to one embodiment, the posterior part 12 of the intravertebral implant 1 is sliding in the anterior inner portion 23. According to one embodiment, the mechanical link between the posterior part 12 and the anterior inner portion 23 is a sliding pivot link. According to one embodiment, the pedicle fixation 2, particularly the pedicle dowel, defines a main axis. According to this embodiment, the posterior part 12 of the intravertebral implant 1 can move in rotation and in translation along said main axis in the anterior inner portion 23 of the pedicle fixation 2.

Advantageously, the anterior portion 23 enables the expansion of the intravertebral implant 1 independently of the anchoring of the pedicle fixation 2 in the vertebral pedicle. Indeed, the degree of freedom in translation along the main axis of the pedicle fixation 2 makes it possible not to constrain the positioning (i.e. the advance due to deployment) of the intravertebral implant 1 in the vertebral body. Furthermore, the degree of freedom in rotation about the main axis of the pedicle fixation 2 makes it possible not to constrain the direction of expansion of the intravertebral implant 1. As such, the intravertebral implant 1, when deployed, adapts the deployment position thereof according to the medium wherein it is deployed (i.e. the vertebral body).

According to one embodiment, the anterior inner portion 23 does not comprise an outer thread. According to one embodiment, the anterior inner portion 23 and the intravertebral implant 1 are not screwed.

Figure 8C:
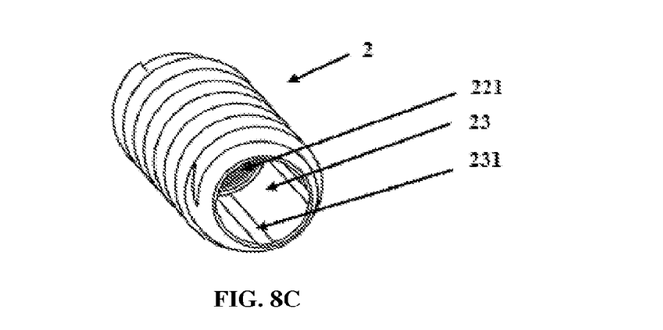
FIG. 8C is a perspective view of the pedicle fixation particularly illustrating the anterior inner portion according to one embodiment of the present invention.

According to one embodiment, the anterior inner portion 23 further comprises at least one groove 231, as represented in FIG. 8C. According to one embodiment, the anterior inner portion 23 comprises at least one axial groove (i.e. a groove parallel with the z axis). According to one embodiment, the anterior inner portion 23 comprises at least one transverse groove (i.e. perpendicular to the z axis). According to one embodiment, the anterior inner portion 23 comprises at least one oblique groove 231.

According to one embodiment, the anterior inner portion 23 comprises at least one axial and/or transverse and/or oblique groove 231. According to one embodiment, the at least one groove 231 comprises a non-constant cross-section. According to one embodiment, the anterior inner portion 23 comprises at least 2, 3, 4, 5, 6, 7, 8, 9, 10 grooves 231. According to one embodiment, the grooves are regularly distributed on the inner surface of the anterior portion 23. According to one embodiment, the pedicle fixation 2 comprises at least one notch 24, or any other means within the scope of those skilled in the art, suitable for rotating the pedicle fixation 2, using an insertion instrument 5.

Posterior Element

Figure 4:
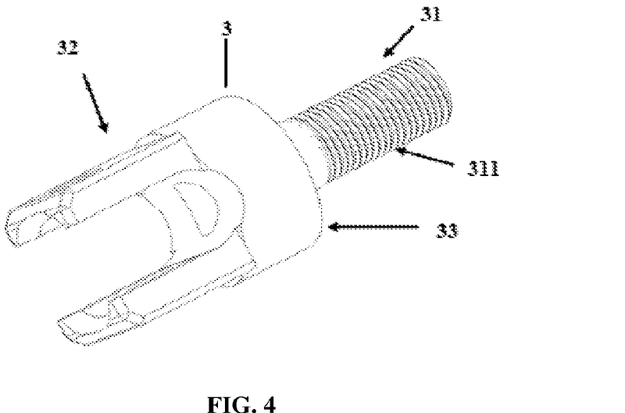
FIG. 4 is a perspective view of the posterior element according to one embodiment of the present invention.

As represented in FIG. 4, the posterior element 3 according to the present invention comprises an anterior portion 31 consisting of a rod, preferably a threaded rod 311 engaging with the internal thread 221 of the pedicle fixation 2, thus enabling the fixation of the posterior element 3 to the pedicle fixation 2. The posterior element 3 also comprises a posterior portion 32, external to the vertebra 4, the geometry whereof makes it possible to carry out assembly functions with complementary posterior fixation elements known to those skilled in the art such as rods or artificial ligaments. Any other assembly configuration with other systems known to those skilled in the art can be envisaged. The posterior element 3 also comprises a bearing surface 33 against bone tissue or against the posterior portion of the pedicle fixation 2, according to the choice made by the operator and/or the penetration of the pedicle fixation 2 in the pedicle bone.

Operation

Figure 5:
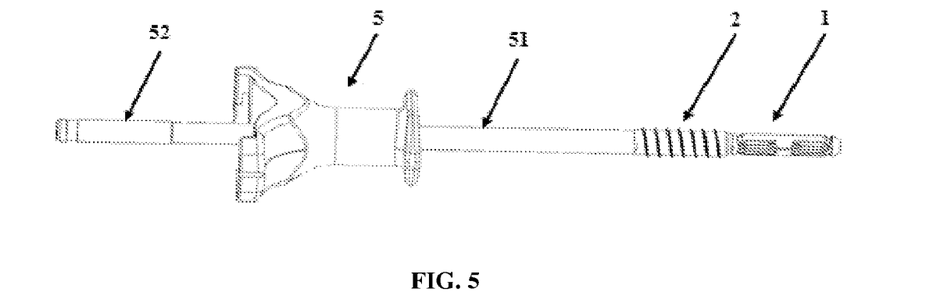
FIG. 5 is a side view of the implant system according to one embodiment of the present invention, mounted on an instrument suitable for the insertion of the implant system.
Figure 6A:
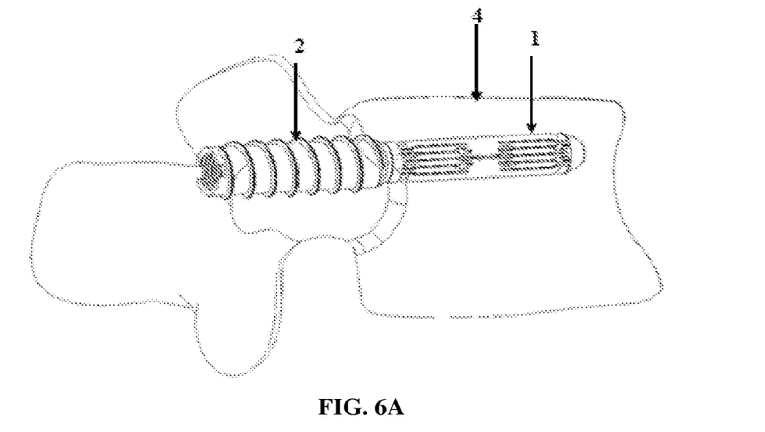
FIG. 6A is a side view of the implant system, according to one embodiment of the present invention, placed in a vertebra; said vertebra being represented as transparent, visible merely by the outlines thereof.
Figure 6B:
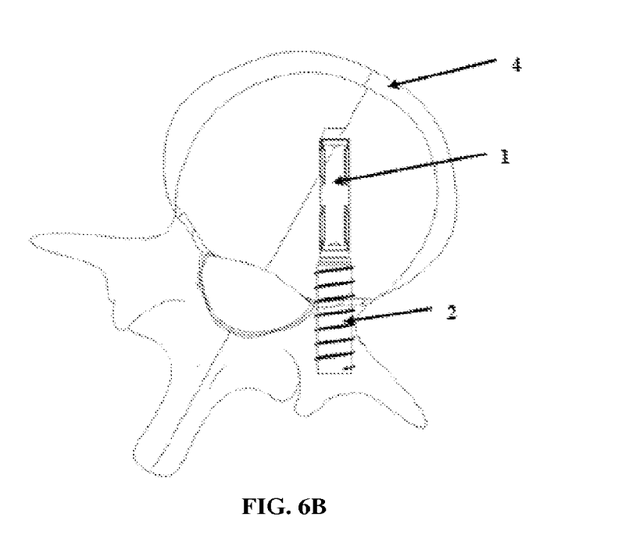
FIG. 6B is a top view of the implant system, according to one embodiment of the present invention, placed in a vertebra; said vertebra being represented as transparent, visible merely by the outlines thereof.

After the creation of an approach and the boring of the vertebral pedicle, the implant system comprising the pedicle fixation 2 and the vertebral implant 1 wherein the posterior part 12 is inserted in the anterior inner portion 23 of the pedicle fixation 2 is inserted, and then screwed, into the pedicle using an insertion instrument 5, as represented in FIG. 5. Said insertion instrument 5 comprises a working cannula 51 rotatably secured (i.e. connected) to the pedicle fixation 2 by means of the notches 24 for screwing the pedicle fixation 2 in the pedicle. Said insertion instrument 5 also comprises an expansion tube 52 situated along the main axis of the insertion instrument 5 and it is configured to traverse at least the length of the posterior inner portion 22. The expansion tube 52 is secured (i.e. connected) to the posterior part 12 of the intravertebral implant 1, and particularly secured to the central traction tube 13 of the intravertebral implant 1. The insertion depth of the implant system is controlled by the screwing of the external thread 21 of the pedicle fixation 2 in the bone tissue, so as to position the intravertebral implant 1 optimally in the vertebral body. The positioning of the intravertebral implant 1 in axial rotation is controlled by the operator independently of the insertion of the pedicle fixation 2, using the tube 52 so as to retain an expansion plane, for example a cranio-caudal expansion plane of the intravertebral implant 1 regardless of the screwing angle obtained during the insertion of the pedicle fixation 2. As represented in FIGS. 6A, 6B, 10A and 10B, the intravertebral implant system according to the present invention is inserted through a vertebral pedicle, the intravertebral implant 1 then being situated in the vertebral body and the pedicle fixation 2 being anchored in the pedicle.

According to one embodiment, after insertion of the implant system, the pedicle fixation 2 is securely fixed in the pedicle and the intravertebral implant 1 is partially secured to the pedicle fixation 2 by the cylindrical posterior part 12 thereof. Indeed, the cylindrical posterior part 12 is inserted into the anterior inner portion 23 thus locking the rotation movements about the y and x axes and locking the translations along said x and y axes. For this reason, these locked degrees of freedom ensure partial securing between the cylindrical posterior part 12 inserted into the anterior inner portion 23. The term securing denotes the locking of all the degrees of freedom between the pedicle fixation 2 and the intravertebral implant 1. The term partial securing denotes the locking of at least one degree of freedom between these two parts. The pedicle fixation 2 then abuts on the shoulder 121. As such, the intravertebral implant 1 has an additional support point in the pedicle. According to one embodiment, the vertebral implant 1 is not secured to the pedicle fixation 2 by screwing. According to one embodiment, the posterior part 12 of the intravertebral implant 1 assembled with the pedicle fixation 2 does not traverse either side of the pedicle fixation 2. According to one embodiment, the posterior part 12 of the vertebral implant 1 is mounted in the anterior inner portion 23 of the pedicle fixation 2.

Figure 7A:
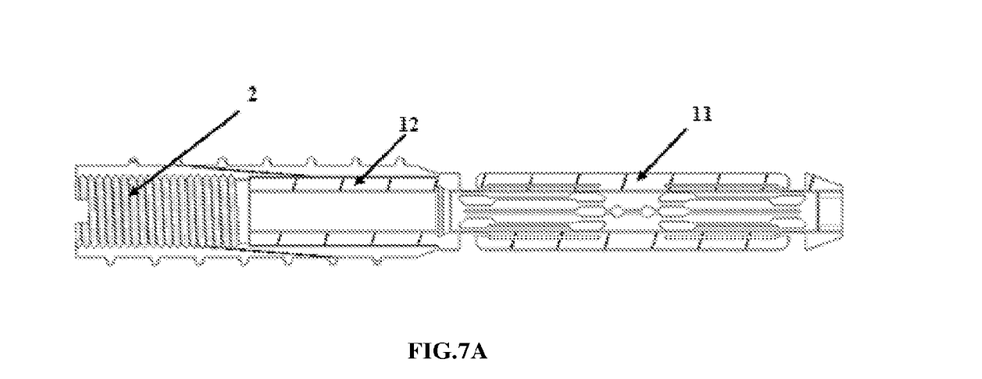
FIG. 7A is a sectional view of the implant system according to one embodiment of the present invention, prior to expansion of the anterior part of the implant.
Figure 7B:
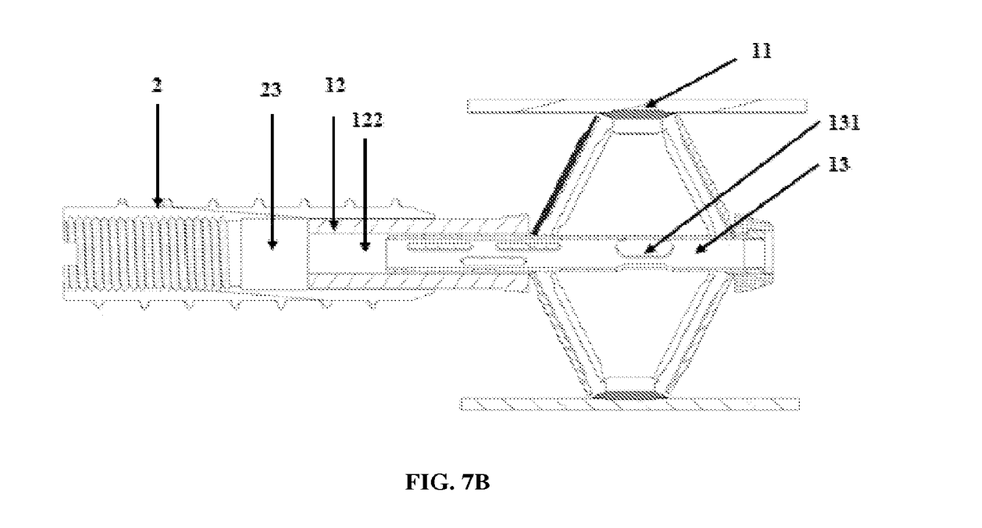
FIG. 7B is a sectional view of the implant system according to one embodiment of the present invention, after expansion of the anterior part of the implant.

As represented in FIGS. 7A and 7B, the expansion of the intravertebral implant 1 is performed by pulling on the central traction tube 13, by means of the tube 52 of the insertion instrument 5 (not shown in the figures). The central traction tube 13 can slide unidirectionally in the posterior part 12 of the implant 1 so as to enable deployment while preventing removal. Pulling the central traction tube 13 enables the deployment of the intravertebral implant 1 by moving the anterior and posterior ends of the anterior part 11 closer together. According to one embodiment, the deployment makes it possible to separate the plates in the vertebral body. This expansion in the vertebral body induces the anterior displacement of the implant: the anterior part 11 of the expandable implant slides through the anterior inner portion 23 so that the anterior part 11 of the intravertebral implant is adapted optimally to the environment wherein it is deployed. Advantageously, the sliding link between the posterior inner portion 23 of the pedicle fixation 2 and the posterior part 12 of the implant 1 is suitable for adapting the position of the intravertebral implant 1 deployed in the vertebral body independently of the position of the pedicle fixation 2.

As represented in FIG. 7B, the posterior part 12 can slide freely in an anterior inner portion 23, without however coming out thereof in order to provide permanent additional support, so as not to constrain the deployment of the intravertebral implant in a position dependent on the location of the pedicle fixation 2 in the pedicle. Indeed, the anterior inner portion 23 is configured to lock the translations and rotations of the intravertebral implant 1 along the x and y axes of the pedicle fixation 2, and enable the translation and rotation along the main axis of the pedicle fixation 2 (i.e. the z axis).

According to one embodiment, the dimensions of the posterior part 12 of the implant 1 are such that, once the posterior part 12 has been inserted into the anterior inner portion 23, the implant 1 can no longer be extracted from the pedicle fixation when it is implanted. The longitudinal dimension of the anterior inner portion 23 is sufficiently long so that the posterior part 12 remains inserted and partially secured to said anterior inner portion 23 during deployment. According to one embodiment, the length of the anterior inner portion 23 is indeed between 1 and 20 mm or between 5 and 15 mm.

According to this embodiment, the intravertebral implant 1 is free in axial rotation and in anterior translation with respect to the pedicle fixation 2. The deployment of the intravertebral implant 1 thus takes place only on the basis of the intravertebral bone environment which determines for the extendable anterior part 11 of the intravertebral implant 1 the orientation and depth of deployment of said extendable part. According to one embodiment, the intravertebral implant, and particularly the posterior part 12 thereof, can be moved along one, two, three, four, five degrees of freedom, preferentially two degrees of freedom, more preferentially one degree of freedom in rotation and one degree of freedom in translation, in the anterior inner portion 23. According to one embodiment, the intravertebral implant 1, and particularly the posterior part 12 thereof, can move in rotation and in translation along the z axis in the anterior inner portion 23.

According to one embodiment, after the expansion of the intravertebral implant 1, the rotation and translation along z between the intravertebral implant and the pedicle fixation are locked, thus securing the expandable intravertebral implant 1 to the pedicle fixation 2.

According to one embodiment, the anterior part 11 of the intravertebral implant 1 is stabilised in the expansion position by injecting a filling material into the vertebra 4, via the at least one through hole 131. The filling material is injected by means of an injector through the pedicle fixation 2, the cylindrical recess 122 of the posterior part 12 of the implant 1 and the hollow traction tube 13, up to the anterior part 11 of the implant 1.

According to one embodiment, the posterior part 12 of the intravertebral implant 1 is secured to the pedicle fixation 2 by locking the relative movements of the posterior portion 12 with respect to the pedicle fixation 2 using securing means.

According to one embodiment, as illustrated in FIG. 8A, the posterior part 12 of the intravertebral implant 1 is secured in the pedicle fixation 2 by injecting a filling material. The filling material is injected through the posterior inner portion 22 into the cylindrical recess 122 and into the at least one through hole 124 so as to come into contact with the inner surface of the anterior inner portion 23. Advantageously, the posterior portion 128 comprises a peripheral chamber 123 wherein the at least one through hole 124 opens. As such, the filling material fills the at least one through hole 124 and the peripheral chamber 123 in order to distribute the filling material at the interface between the posterior portion 128 and the anterior inner portion 23 and thus increase the contact surface area. In order to reinforce the securing further, the anterior inner portion 23 comprises at least one groove 231 and the filling material injected into the cylindrical recess 122 fills the at least one through hole 124, the peripheral chamber 123 and the at least one groove 231 of the anterior inner portion 23. Advantageously, the solidification of the filling material in the at least one axial groove 231 reinforces the securing according to the degree of freedom in rotation about the z axis. Advantageously, the solidification of the filling material in the at least one transverse groove 231 reinforces the securing according to the degree of freedom in translation along the z axis. Advantageously, the solidification of the filling material in the at least one oblique groove 231 reinforces the securing along the degrees of freedom in translation and rotation along the z axis. Advantageously, the solidification of the filling material in the at least one groove 231 of non-constant cross-section reinforces the securing according to the degree of freedom in translation and rotation along the z axis. According to one embodiment, the grooves 231 further enable the injection of the filling material to the anterior inner portion 23 reinforcing the securing further. According to one embodiment, the filling material injected into the cylindrical recess 122 fills the at least one through hole 124, the peripheral chamber 123 and the at least one groove 231 of the anterior inner portion 23, and all or part of the volume of the anterior inner portion 23. Advantageously, the peripheral chamber 123 makes it possible to reach the grooves 231 independently of the orientation of the intravertebral implant 1, and particularly of the orientation of the posterior portion 128, in the pedicle fixation 2.

According to one embodiment, as illustrated in FIG. 9A, the posterior part 12 of the intravertebral implant 1 is secured in the pedicle fixation 2 by means of a conical expansion cap 6. Said conical cap comprises an external thread and a flared posterior end. Said cap 6 is inserted through the posterior inner portion 22, optionally after injecting cement into the vertebra via the through hole 131, and targeted in the internal thread 126 of the posterior portion 128. When the conical cap 6 is screwed into the internal thread 126 of the posterior portion 128, the flared end of the cap abuts against the flared end of the posterior portion 127 causing the radial deployment of the posterior portion, enabled by means of the slots 125. Advantageously, the radial deployment of the posterior portion 128 in the anterior inner portion 23 secures the posterior part 12 of the intravertebral implant 1 in the pedicle fixation 2 by pressing.

According to one embodiment, once the intravertebral implant 1 has been deployed, secured to the pedicle fixation 2 and stabilised, if required by means of the injection of specially adapted bone cement or substitute, it is then possible to secure (i.e. connect) to the pedicle fixation 2—intravertebral implant 1 assembly the posterior element 3 by merely screwing and fastening same in the posterior inner portion 22 of the pedicle fixation 2. In this embodiment, the posterior element 3 is at least partially external to the vertebra 4 and is then capable of receiving posterior fixation elements such as rods or artificial ligament systems or any other means for stabilising the vertebral facture known to those skilled in the art.

The present invention also relates to a method for treating vertebral fractures comprising:
  insertion of an implant system according to the invention wherein the posterior part 12 is already inserted into the anterior inner portion 23 in a vertebra 4 and screwing of the pedicle fixation 2 in the vertebral pedicle by means of the external thread 21;
  expansion of the anterior part 11 of the intravertebral implant 1, particularly by pulling the central traction tube 13;
  positioning of the anterior part 11 of the intravertebral implant in the vertebral body enabled by the movement of the posterior part 12 of the intravertebral implant 1 in translation and rotation, along the main axis of the pedicle fixation 2, in the anterior inner portion 23 of the pedicle fixation 2;
  optionally, injection of a filling material into the vertebral body via a through hole 131 to stabilise the anterior part 11 of the intravertebral implant 1; and
  optionally, securing of the posterior part 12 in the anterior inner portion 23.

The invention claimed is:

1. A system for stabilizing, reinforcing or repairing a fracture of a vertebral body including a pedicle, the system comprising:
  an intravertebral implant comprising an anterior end element and a plate comprising a planar bearing surface;
  a pedicle fixation coupled to the intravertebral implant and comprising a hollow sleeve defining a main axis, wherein the pedicle fixation is configured to be secured to the pedicle to control an insertion depth of the intravertebral implant within the vertebral body along the main axis; and
  a central traction member movably disposed within the hollow sleeve of the pedicle fixation and configured to receive a pulling input to proximally translate the central traction member along the main axis to cause the anterior end element to be moved towards the pedicle fixation, thereby causing expansion of the intravertebral implant by the planar bearing surface being moved away from the main axis of the intravertebral implant in only a cranio-caudal expansion plane.

2. The system of claim 1, wherein the central traction member is rotatable within the hollow sleeve about the main axis.

3. The system of claim 1, wherein the planar bearing surface is configured to be parallel to the main axis for at least a portion of movement away from the main axis of the intravertebral implant.

4. The system of claim 1, wherein the hollow sleeve of the pedicle fixation further comprises external threads.

5. The system of claim 4, further comprising an insertion instrument removably and rotatably coupled to the pedicle fixation and configured to rotate the hollow sleeve to screw the external threads in the pedicle.

6. The system of claim 1, further comprising an expansion instrument configured to be coupled to and provide the pulling input to the central traction member so as to proximally translate the central traction member relative to the pedicle fixation along the main axis.

7. The system of claim 1, wherein the intravertebral implant configured to be locked relative to the pedicle fixation in six degrees of freedom.

8. The system of claim 1, wherein the intravertebral implant and the pedicle fixation are not threadably engaged.

9. A system for stabilizing, reinforcing or repairing a fracture of a vertebral body, the system comprising:
an intravertebral implant comprising an anterior end element and exactly two plates, wherein the exactly two plates are a first plate comprising a first planar bearing surface and a second plate comprising a second planar bearing surface;
a pedicle fixation coupled to the intravertebral implant and comprising a sleeve having external threads and being hollow to define a passageway along a main axis, wherein screwing of the external threads in a pedicle is configured to control an insertion depth of the intravertebral implant within the vertebral body; and
a central traction member disposed within the passageway along the main axis and rotatable relative to the sleeve of the pedicle fixation, wherein the central traction member is configured to receive a pulling input for the central traction member to cause the anterior end element to be moved towards the pedicle fixation, thereby causing expansion of the intravertebral implant by the first planar bearing surface and the second planar bearing surface being moved away from the main axis of the intravertebral implant in only a cranio-caudal expansion plane.

10. The system of claim 9, further comprising an insertion instrument removably and rotatably coupled to the pedicle fixation and configured to rotate the sleeve to screw the external threads in the pedicle.

11. The system of claim 10, further comprising an expansion instrument configured to be coupled to and provide the pulling input to the central traction member so as to move the central traction member relative to the pedicle fixation.

12. The system of claim 9, wherein the intravertebral implant configured to be locked relative to the pedicle fixation in six degrees of freedom.

13. The system of claim 9, further comprising:
a posterior element configured to be coupled to the pedicle fixation; and
a rod configured to be coupled to the posterior element.

14. The system of claim 9, wherein the central traction member is a tube defining ports configured to direct curable material to within the vertebral body between the first plate and the second plate.

15. The system of claim 9, wherein the intravertebral implant and the pedicle fixation are not threadably engaged.

* * * * *